US009170209B1

(12) United States Patent
Chang et al.

(10) Patent No.: US 9,170,209 B1
(45) Date of Patent: *Oct. 27, 2015

(54) INSPECTION GUIDED OVERLAY METROLOGY

(71) Applicant: KLA-Tencor Corporation, Milpitas, CA (US)

(72) Inventors: Ellis Chang, Saratoga, CA (US); Amir Widmann, Doar Na (IL); Allen Park, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,193

(22) Filed: Oct. 14, 2013

Related U.S. Application Data (63) Continuation of application No. 12/984,679, filed on Jan. 5, 2011, now Pat. No. 8,559,001.

(60) Provisional application No. 61/293,706, filed on Jan. 11, 2010.

(51) Int. Cl.
| | |
|---|---|
| G01N 21/00 | (2006.01) |
| G01R 31/26 | (2014.01) |
| G01N 21/95 | (2006.01) |
| H01L 21/66 | (2006.01) |
| G01N 21/956 | (2006.01) |
| G03F 7/20 | (2006.01) |
| G01N 21/88 | (2006.01) |

(52) U.S. Cl.
CPC ...... *G01N 21/9501* (2013.01); *G01N 21/95607* (2013.01); *G03F 7/7065* (2013.01); *H01L 22/12* (2013.01); *G01N 2021/8822* (2013.01); *H01L 2924/0002* (2013.01)

(58) Field of Classification Search
CPC ............ G01N 21/9501; G01N 21/95607; G03F 7/70633; G03F 7/7065; H01L 22/12
See application file for complete search history.

(56) References Cited

U.S. PATENT DOCUMENTS

| | | |
|---|---|---|
| 6,673,637 B2 | 1/2004 | Wack et al. |
| 6,940,592 B2 | 9/2005 | Borden et al. |
| 7,445,945 B1 | 11/2008 | Markie et al. |
| 7,570,796 B2 | 8/2009 | Zafar et al. |
| 7,629,259 B2 | 12/2009 | Sadjadi |
| 7,676,077 B2 | 3/2010 | Kulkarni et al. |
| 7,804,994 B2 | 9/2010 | Adel et al. |
| 8,073,240 B2 | 12/2011 | Fischer et al. |

(Continued)

*Primary Examiner* — Kara E Geisel
*Assistant Examiner* — Dominic J Bologna
(74) *Attorney, Agent, or Firm* — Suiter Swantz pc llo (57) ABSTRACT

Inspection guided overlay metrology may include performing a pattern search in order to identify a predetermined pattern on a semiconductor wafer, generating a care area for all instances of the predetermined pattern on the semiconductor wafer, identifying defects within generated care areas by performing an inspection scan of each of the generated care areas, wherein the inspection scan includes a low-threshold or a high sensitivity inspection scan, identifying overlay sites of the predetermined pattern of the semiconductor wafer having a measured overlay error larger than a selected overlay specification utilizing a defect inspection technique, comparing location data of the identified defects of a generated care area to location data of the identified overlay sites within the generated care area in order to identify one or more locations wherein the defects are proximate to the identified overlay sites, and generating a metrology sampling plan based on the identified locations.

24 Claims, 4 Drawing Sheets

(56) References Cited

U.S. PATENT DOCUMENTS

| | | |
|---|---|---|
| 8,126,255 B2 | 2/2012 | Bhaskar et al. |
| 8,559,001 B2 * | 10/2013 | Chang et al. ............... 356/237.5 |
| 2002/0042664 A1 * | 4/2002 | Kikuchi ........................ 700/114 |
| 2002/0193899 A1 | 12/2002 | Shanmugasundram et al. |
| 2004/0126004 A1 * | 7/2004 | Kikuchi ........................ 382/141 |
| 2005/0021272 A1 | 1/2005 | Jenkins et al. |
| 2006/0030061 A1 | 2/2006 | DiBase |
| 2006/0074503 A1 | 4/2006 | Purdy |
| 2006/0291714 A1 * | 12/2006 | Wu et al. ........................ 382/149 |
| 2007/0156379 A1 * | 7/2007 | Kulkarni et al. ................ 703/14 |
| 2007/0288219 A1 * | 12/2007 | Zafar et al. ....................... 703/14 |
| 2008/0279444 A1 * | 11/2008 | Fischer et al. ................ 382/145 |
| 2009/0043527 A1 | 2/2009 | Park et al. |
| 2009/0080759 A1 | 3/2009 | Bhaskar et al. |

\* cited by examiner

INSPECTION GUIDED OVERLAY METROLOGY

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation patent application of United States Provisional Patent Application entitled INSPECTION GUIDED OVERLAY METROLOGY, naming Ellis Chang, Amir Widmann and Allen Park as inventors, filed Jan. 5, 2011, application Ser. No. 12/984,679, which constitutes a regular (non-provisional) patent application of United States Provisional Patent Application entitled ENABLING TECHNOLOGIES AND APPLICATION OF DESIGN AND INSPECTION FOR OVERLAY METROLOGY AND SAMPLING IMPROVEMENT, naming Ellis Chang, Amir Widmann, Allen Park, and Chun-Chieh Damian Chen as inventors, filed Jan. 11, 2010, Application Ser. No. 61/293,706.

TECHNICAL FIELD

The present invention generally relates to a methods and systems for generating a metrology sampling plan, and more particularly to inspection guided overlay metrology of a semiconductor wafer.

BACKGROUND

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etching, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Accordingly, much work in the inspection field has been devoted to designing inspection systems that can detect defects having sizes that were previously negligible. Typical inspection processes detect defects by comparing similar semiconductor device areas on a wafer. The differences detected between the two device areas can either be a defect, which can cause a device to function improperly, or a nuisance, which will not affect system operations. An integral phase of semiconductor wafer inspection involves optimizing the settings, commonly referred to as the "recipe," of an inspection device so that it can accurately distinguish defects from nuisances. After potential defects are found by an inspection system, the wafer is typically transferred to a review tool for classification of the defects. However, classification of the defects requires optimizing the settings of the review tool, also referred to as a "recipe", so that the review tool can adequately classify the potential defects or determine that the potential defects are nuisances or false defects.

In sum, analysis of the defects on a particular wafer lot requires setting up and optimizing a recipe for an inspection tool and setting up a different recipe for the review tool. Setting up two recipes for two different tools is time consuming and complex.

Inspection for many different types of defects has also become more important recently. For instance, in order to use inspection results to monitor and correct semiconductor fabrication processes, it is often necessary to know what types of defects are present on a wafer. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined from currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

An overlay measurement generally specifies how accurately a first patterned layer aligns with respect to a second patterned layer disposed above or below it or how accurately a first pattern aligns with respect to a second pattern disposed on the same layer. The overlay error is typically determined with an overlay target having structures formed on one or more layers of a work piece (e.g., semiconductor wafer). The structures may take the form of gratings, and these gratings may be periodic. If the two layers or patterns are properly formed, then the structure on one layer or pattern tends to be aligned relative to the structure on the other layer or pattern. If the two layers or patterns are not properly formed, then the structure on one layer or pattern tends to be offset or misaligned relative to the structure on the other layer or pattern. Overlay error is the misalignment between any of the patterns used at different stages of semiconductor integrated circuit manufacturing. Conventionally, understanding of the variation across die and wafer are limited to the fixed sampling and hence overlay error is detected only for the known selected sites.

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on the wafer such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Therefore, the sampling plan of the metrology process can significantly affect the meaningfulness and usefulness of the metrology results.

There are, however, a number of disadvantages to currently used metrology sampling plans. For instance, traditional metrology sampling approaches are based on fixed locations on the wafer, which may represent samples across the wafer or may be based on previously known problem areas on the wafer. Measurements may then be performed on given sites until the fixed sample plan is adjusted (e.g., manually). Therefore, one of the disadvantages of currently used metrology sampling plans is that the fixed sites that are sampled during metrology may not be sensitive to subtle variations in the process. For example, in the event that critical dimension (CD) varies in the areas on the wafer that the fixed sampling does not cover, an important excursion may be missed.

Accordingly, it may be desirable to provide a method and/or system which combine advanced defect inspection with overlay metrology in order to provide improved coverage and sampling efficiency in a process performed on a semiconductor wafer.

SUMMARY

A method for inspection guided overlay metrology is disclosed. In one aspect, the method for inspection guided overlay metrology may include, but is not limited to, performing a pattern search in order to identify one or more instances of a predetermined pattern on a semiconductor wafer, generating a care area for each of the one or more instances of the predetermined pattern on the semiconductor wafer, identifying one or more defects within each of the one or more generated care areas by performing an inspection scan of each of the one or more generated care areas, wherein the inspection scan includes a low-threshold inspection scan or a high sensitivity inspection scan, identifying one or more overlay sites of at least some of the one or more instances of the predetermined pattern of the semiconductor wafer having a measured overlay error larger than a selected overlay specification utilizing a defect inspection technique, comparing location data of the one or more identified defects of a generated care area to location data of the one or more identified overlay sites within the generated care area in order to identify one or more locations wherein the one or more defects are proximate to the one or more identified overlay sites, and generating a metrology sampling plan based on the identified one or more locations wherein the one or more defects are proximate to the one or more identified overlay sites.

A system for inspection guided overlay metrology is disclosed. In one aspect, the system for inspection guided overlay metrology may include, but is not limited to, an inspection system configured to detect defects on a semiconductor wafer, a metrology system configured to measure overlay error at one or more locations of a selected pattern on a semiconductor wafer, and a computer system configured to: perform a pattern search in order to identify one or more instances of a predetermined pattern on a semiconductor wafer, generate a care area for each of the one or more instances of the predetermined pattern on the semiconductor wafer, identify one or more defects within each of the one or more generated care areas by performing an inspection scan of each of the one or more generated care areas, wherein the inspection scan includes a low-threshold inspection scan or a high sensitivity inspection scan, identify one or more overlay sites of at least some of the one or more instances of the predetermined pattern of the semiconductor wafer having a measured overlay error larger than a selected overlay specification utilizing a defect inspection technique, compare location data of the one or more identified defects of a generated care area to location data of the one or more identified overlay sites within the generated care area in order to identify one or more locations wherein the one or more defects are proximate to the one or more identified overlay sites, and generate a metrology sampling plan based on the identified one or more locations wherein the one or more defects are proximate to the one or more identified overlay sites.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1 through 4B, a method and system for inspection driven overlay metrology is described in accordance with the present disclosure. Employing a combined defect inspection and overlay metrology technique may aid in optimizing overall semiconductor defect and overlay measurement sensitivity and sampling coverage on a semiconductor wafers. Conventionally overlay sampling is carried out at only fixed locations of a semiconductor wafer. The present invention is directed at providing a method and system for providing overlay sampling at dynamic locations of the semiconductor wafer, thereby extending the aerial extent of overlay error and abnormality detection. One aspect of the present invention is the use of an inspection signal associated with detected wafer anomalies as a mechanism for initially detecting overlay metrology sites displaying overlay error that is greater than a selected overlay error value. The predetermined patterns with which these potential overlay sites reside may then be searched for and identified in other areas of the semiconductor wafer. Upon identifying these overlay sites at other instances of the selected pattern a low-threshold inspection scan may be performed for a care area generated to encompass a selected region containing the identified overlay sites of the identified predetermined patterns. The inspection scan is implemented in order to identify defects within the generated care area. After the inspection scan, the positions of the detected defects may be compared to the positions of potential overlay sites within a given care area. After comparison, an overlay metrology plan may be generated which acts to instruct a metrology system to perform metrology measurements at positions where a detected defect substantially coincides with a potential overlay site. Moreover, this overly metrology plan may be provided to an overlay metrology system, which then carries out the overlay metrology plan.

Figure 1:
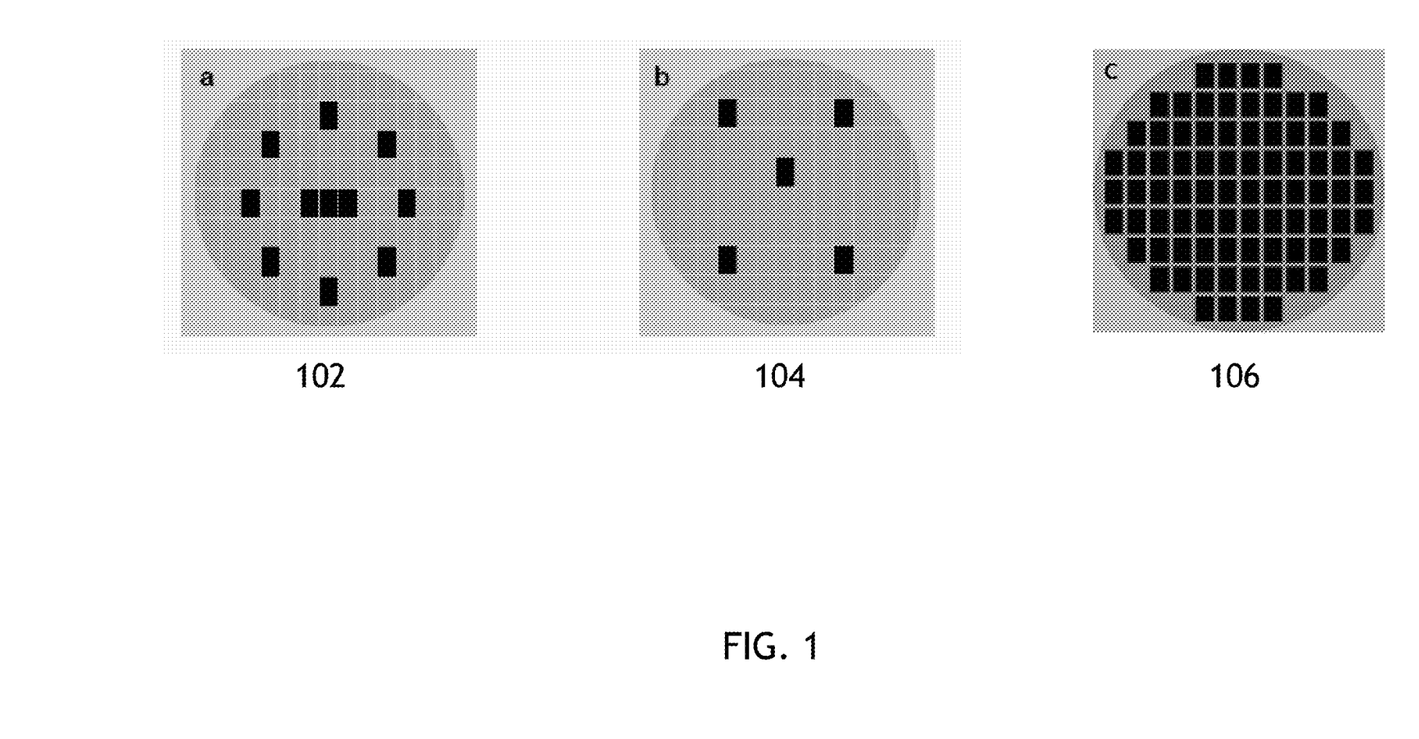
FIG. 1 illustrates a series of exemplary overlay metrology sampling plans.

It is contemplated that the method and system of the present invention will provide a mechanism for overlay metrology for advanced nodes, such as 32 nm and 22 nm devices, which require a total measurement uncertainty (TMU) of 0.4 nm or less. In the case of conventional sampling methods, there exists an increased chance missing overlay error across a die and or wafer. In addition to decreased sensitivity, the conventional overlay metrology tools and methods are time consuming. By combining defect inspection with overlay metrology, the defect detection sensitivity and sampling coverage are optimized. FIG. 1 illustrates a series of sampling plans for overlay error measurement of a semiconductor wafer 206. Sampling plan 102 illustrates the sampling plan at a mask step, wherein the darkened regions represent sampling areas of the semiconductor wafer 206. Sampling plan 104 represents an additional overlay measurement sampling plan at a mask step. Moreover, sampling plan 106 represents the desired sampling plan that may be carried out using an inspection driven metrology process and system of the present invention.

As used throughout the present disclosure, the term "wafer" generally refers to substrates formed of a semiconductor or non-semiconductor material. For example, a semiconductor or non-semiconductor material include, but are not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for improved defect detection for overlay error of semiconductor target such as a reticle, which may also be commonly referred to as a mask or a photo mask. Many different types of reticles are known in the art, and the terms "reticle," "mask," and "photo mask" as used herein are intended to encompass all types of reticles known in the art.

A semiconductor chip design known as the "floorplan" contains the placement information for repeating structures known as cells. This information can be extracted from the physical design of a chip usually stored in GDSII or OASIS file formats. A motivation for this application is the classification of cell repeater defects. For purposes of discovering and classification of cell level repeater defects, the analysis tool needs to know only the orientation and location of the cells. The structural behavior or process-design interactions can be a function of the context (surroundings) of a cell. By using the floor plan, the analysis proposed can automatically tell which cell types are having problems, what the location within the cell is (coordinates of the polygons having problems) and the context (what are the adjacent cells) in which the cell is having problems if this is a factor.

Each defect found by an inspector for a given wafer would be subjected to the standard cell repeater analysis which is typically done at the die and reticle level. Conventionally repeater analysis is performed across die, across reticle across wafer and wafer to wafer spatial analysis on cell defectivity to identify the signature of die, reticle, wafer and process equipment level phenomenon that interact with the weak structures that are sensitive to process variations.

In other embodiments, an image of a reticle generated by a reticle inspection system is used as design data in the design data space. The reticle is used to print the design data on the wafer. In this manner an image beam image of the reticle is acquired by a high magnification optical reticle inspection system or an electron beam based reticle inspection system respectively. Alternatively the image of the reticle may be an aerial image of the reticle acquired by an aerial imaging reticle inspection system. The image of the reticle may be used as a proxy for the design data in any of the embodiments described herein that use design data to perform one or more steps.

The term "design data" as used in the present disclosure generally refers to the physical design of an integrated circuit and data derived from the physical design through complex simulation or simple geometric and Boolean operations. In addition, an image of a reticle acquired by a reticle inspection system and/or derivatives thereof may be used as a proxy or proxies for the design data. Such a reticle image or a derivative thereof may serve as a substitute for the design layout in any embodiments described herein that uses design data. Design data and design data proxies are described in U.S. patent application Ser. No. 11/561,735 by Kulkarni and Ser. No. 11/561,659 by Zafar et al., both of which were filed on Nov. 20, 2006 and both of which are incorporated herein by reference.

In an additional embodiment, the method includes generating a context map for design data in the design data space based on reticle inspection data acquired for a reticle used to print the design data on the wafer. In this manner reticle inspection data may be included as input to the generation of a context map. The context map may be configured as described further herein (e.g., the context map may include values for one or more attributes of the design data across design data space). The reticle inspection data used to generate the context map may include any suitable reticle inspection data known in the art such as one or more of the reticle images described above. In this embodiment, the reticle inspection data may be used to determine values for one or more attributes of design data printed on the reticle across the reticle and these values may be mapped to design data space to generate the context map.

Figure 2:
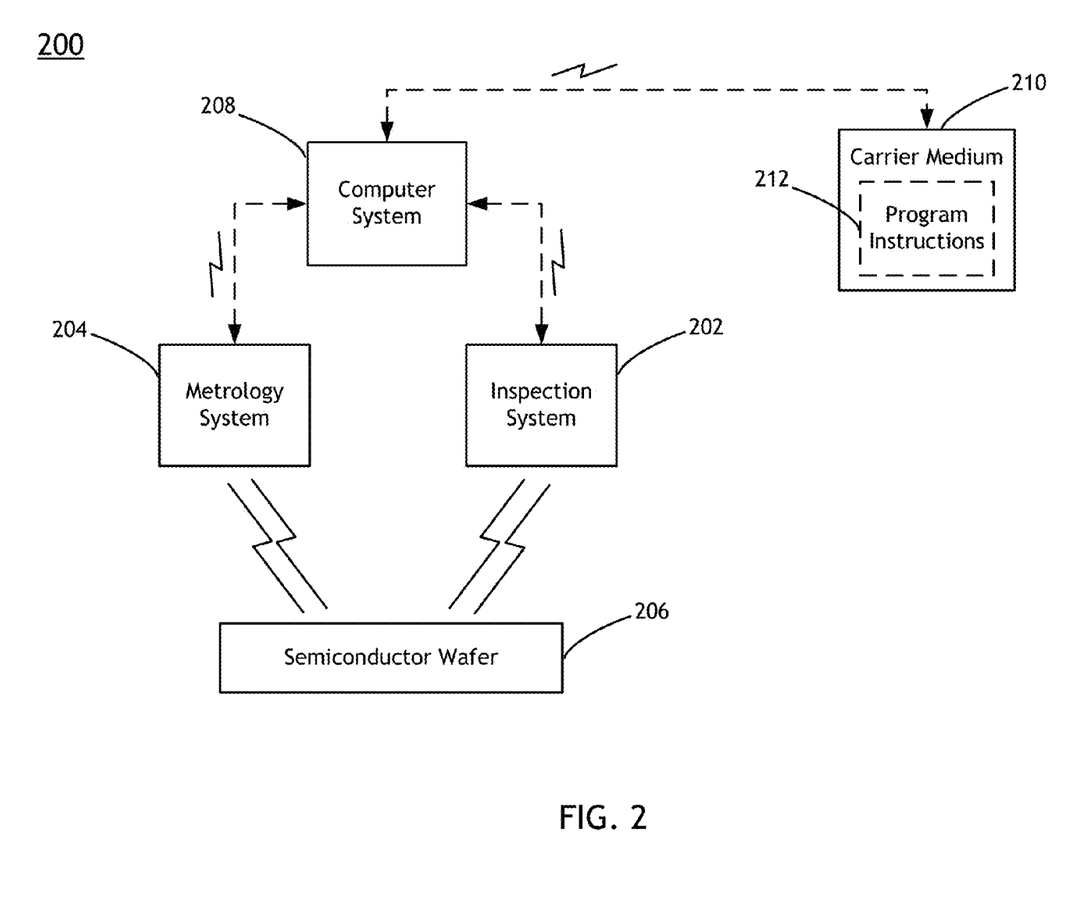
FIG. 2 is a block diagram illustrating a system for inspection guided overlay metrology, in accordance with one embodiment of the present invention.

FIG. 2 illustrates a system 200 for combined defect inspection and overlay metrology which may be utilized to perform the process 100. In one embodiment, the system 200 may include an inspection system 202 configured to detect defects and/or potential overlay metrology sites on a semiconductor wafer 206. The inspection system 202 may include any appropriate inspection system known in the art, such as, but not limited to, a bright-field inspection system, a dark-field inspection system, or an electron beam inspection system. In a further embodiment, the inspection system 202 may be configured to accept instructions from another subsystem of the system 200 in order to dynamically identify defects and/or overlay sites of the semiconductor wafer 206. For instance, the inspection system 202 may accept instructions from a computer system 208 of the system 200. Upon receiving the instructions from the computer system 208, the inspection system 202 may perform an inspection process at the locations of the semiconductor wafer 206 identified in the provided instructions.

In another embodiment, the system 200 may include a metrology system 204 configured to perform overlay metrology at identified locations of the semiconductor wafer 206. The metrology system 204 may include any appropriate metrology system known in the art, such as, but not limited to, critical dimension metrology. In a further embodiment, the metrology system 204 may be configured to accept instructions from another subsystem of the system 200 in order to carry out a desired dynamically designed metrology plan. For instance, the metrology system 204 may accept instructions from a computer system 208 of the system 200. Upon receiving the instructions from the computer system 208, the metrology system 204 may perform overlay metrology measurements at the locations of the semiconductor wafer 206 identified in the provided instructions.

In one embodiment, a computer system 208 of the system 200 may be configured to generate a metrology plan based on a comparison of defect locations and identified metrology sites of a given care area on a semiconductor wafer 206. The computer system 200 may then transmit instructions to the metrology system 204 which are indicative of the metrology sampling plan. Moreover, the computer system 208 may be configured to generate the metrology sampling plan according to any of the embodiments described herein. The computer system 208 may be configured to perform any other step(s) of any of the method embodiments described herein.

In another embodiment, the computer system 208 may be communicatively coupled to the inspection system 202 or the metrology system 204 in any manner known in the art. For example, the computer system 208 may be coupled to a computer system of the inspection system 202 and a computer system of the metrology system 204. In another example, the inspection system 202 and metrology system 204 may be controlled by a single computer system. In this manner, the computer system of the system 200 may be coupled to a single metrology-inspection computer system. Moreover, the computer system 208 of the system 200 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 208 and other subsystems of the system 200. Moreover, the computer system 208 may send data to external systems via a transmission medium. For instance, the computer system 208 may send a generated metrology plan to a separate metrology system, which exists independently of the described system 200.

The computer system 208 may include, but is not limited to, a personal computer system, mainframe computer system, workstation, image computer, parallel processor, or any other device known in the art. In general, the term "computer system" may be broadly defined to encompass any device having one or more processors, which execute instructions from a memory medium.

Program instructions 212 implementing methods such as those described herein may be transmitted over or stored on carrier medium 210. The carrier medium may be a transmission medium such as a wire, cable, or wireless transmission link. The carrier medium may also include a storage medium such as a read-only memory, a random access memory, a magnetic or optical disk, or a magnetic tape.

The embodiments of the system 200 illustrated in FIG. 2 may be further configured as described herein. In addition, the system 200 may be configured to perform any other step(s) of any of the method embodiments described herein.

Figure 3:
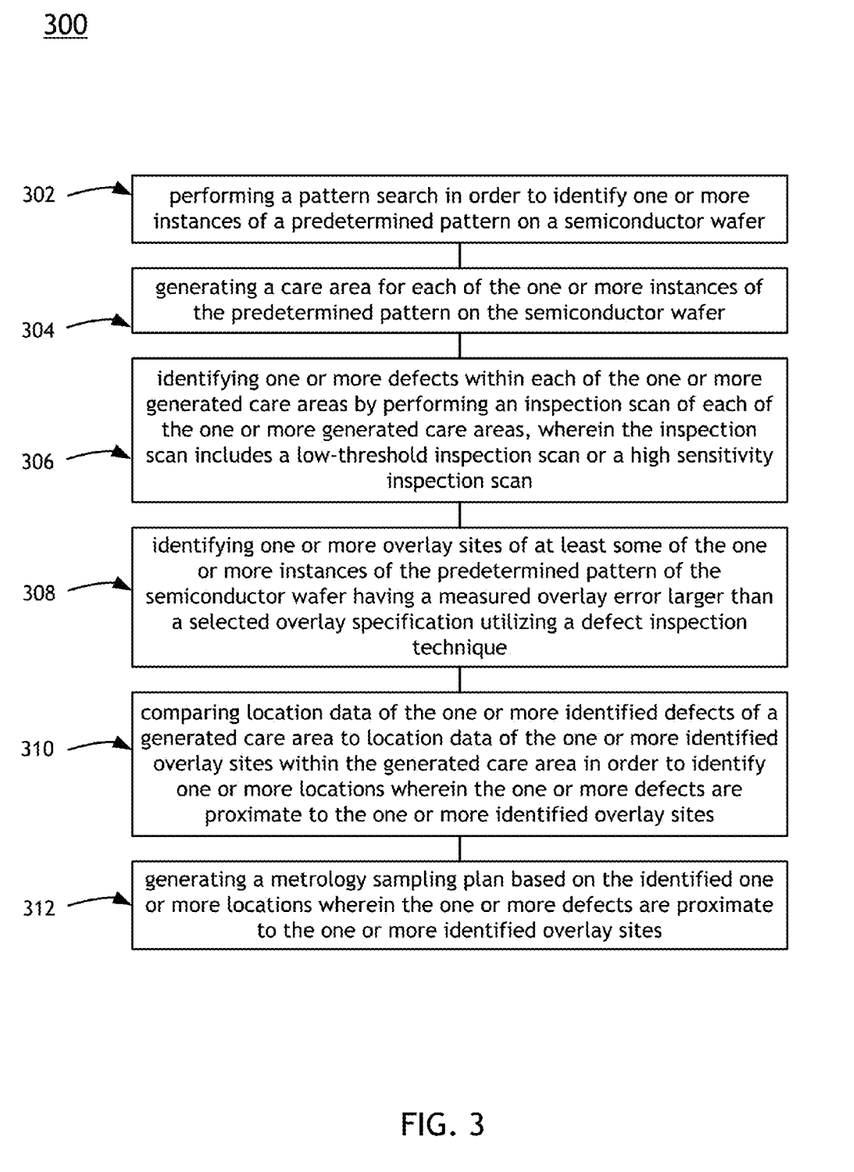
FIG. 3 is a flow diagram illustrating a method for inspection guided overlay metrology, in accordance with one embodiment of the present invention.

FIG. 3 is a flow diagram illustrating steps performed in a computer-implemented method for combined defect inspection and overlay metrology process 300.

In a first step 302, a pattern search may be performed in order to identify the selected predetermined pattern at additional locations of the semiconductor wafer 206.

In one embodiment, a pattern of interest (POI) may be identified by a user. For example, a POI that is selected by a user may be identified on the semiconductor wafer by utilizing data from electronic design automation (EDA) tools, design based binning (DBB), and other knowledge. The DBB may be performed by an inspection system 202, such as a bright field (BF) inspection system configured to perform such binning. For example, information about the design for the wafer such as the critical path information may be generated by an EDA tool. In one such example, the critical path information may be available from EDA tools such as Blaze MO™ Optimization Software commercially available from Blaze DFM, Inc., Sunnyvale, Calif., and tools commercially available from Cadence Design Systems, Inc., San Jose, Calif. Any such information about the design generated by an EDA tool may be used to identify a POI. For example, the POI may be selected as a pattern that forms part of a critical path or is located at or near a critical path on the same layer as the POI or on another layer of the wafer. In addition, the design data may be searched for one or more POIs in any suitable manner. For example, searching the design data for one or more POIs may be performed as described in the above-referenced patent applications by Kulkarni et al. and Zafar et al., which are incorporated by reference. In addition, the POI(s) may be selected or identified using any other method or system described in these patent applications.

In another embodiment, the method includes identifying the predetermined pattern by binning defects detected on the wafer in groups such that portions of design data proximate positions of the defects in each of the groups are at least similar. In this manner, the method may include binning the defects based on the design data proximate the positions of the defects, which may be referred to as DBB. As such, different groups of defects may be located in different portions of the design data and therefore proximate different patterns in the design data. Therefore, one or more attributes of the groups of defects (e.g., number of defects included in each of the groups) may be used to determine patterns that are more susceptible to defects or that exhibit higher defectivity. A pattern that is more susceptible to defects or that exhibits higher defectivity may be selected as the predetermined pattern. Such patterns may, therefore, be more relevant to the yield of the manufacturing process. In this manner, the embodiments described herein may be used for application of design-aware inspection results to identify weak patterns and to provide dynamic CD sampling for such patterns. As such, generating metrology sampling plans as described herein for such patterns may be particularly advantageous since process excursions occurring in these yield relevant patterns are more likely to be detected by metrology performed using such sampling plans compared to sampling plans that are fixed regardless of the inspection results. Binning the defects as described above may be performed as described in detail in the patent applications by Kulkarni et al. and Zafar et al., which are incorporated by reference above.

In a second step 304, a care area may be generated for each instance of the identified predetermined pattern.

In one embodiment, the care areas may be generated via context based inspection (CBI). For example, care area generation may include selecting a region of interest in a full die image. Then, design may be extracted for the selected region of interest. Next, one or more hotspots may be extracted from the design. Moreover, multiple care areas may be generated based on the multiple extracted hot spots. It is further recognized that up to 10 million care area rectangles may be generated per die. Context based inspection is described in U.S. patent application Ser. No. 12/115,832, filed on May 6, 2008, and is incorporated herein by reference. In another embodiment, a care area may be generated for each of the one or more additional locations of the predetermined pattern on the semiconductor wafer based on one or more results of a cell names search process. This method is particularly useful when the areas of inspection are relatively small.

In a third step 306, defects within each care area formed in step 304 may be detected by performing a low-threshold inspection scan or a high sensitivity inspection scan of each care area.

The low-threshold inspection may include any suitable inspection process and any suitable inspection system 202. For example, the inspection results may be acquired using a bright-field (BF) inspection system, dark-field (DF) inspection system or an electron beam inspection system. Moreover, the results of the inspection by the inspection system 202 may include defect locations, defect sizes, images of the defects, or any other output generated by an inspection system. Utilizing low-threshold inspection allows for improved detection of low signal producing defects while also increasing the data collection speed of the inspection process. Moreover, it should be recognized that a unique inspection recipe may utilized for each care area that is inspected by the inspection system 202. The tuning of an inspection recipe to the individual care areas provides for optimized detection of defects of the semiconductor wafer.

The process 300 may include detecting the defects on the semiconductor wafer. For example, the low-threshold inspection may include inspecting sample wafers. For instance, the process 300 may include generating results of an inspection of the wafer by performing inspection of the wafer using the inspection system 202 or a suitable analog. Moreover, the process 100 may include acquiring the results of an inspection of the semiconductor wafer from an inspection system 202 that performed the inspection or from a storage medium (e.g., a storage medium of the inspection system, a fab database or the like) in which the inspection system stored the results of the inspection.

All of the images of the wafer generated using stored image data may also be stored in the arrays of the storage medium any other suitable storage media. For example, in one embodiment, the set of processor nodes may be configured to archive images of the wafer acquired in multiple imaging modes of the inspection system 202. In this manner, whole wafer images generated from image data acquired using multiple imaging modes may be stored on disk. In addition, the embodiments described herein may be configured to perform one or more functions using the archived wafer images. For example, in one embodiment, the archived images may be used for mode selection for an inspection recipe. Such archived images may be used as described further herein to select one or more parameters (e.g., an optical mode) of an inspection system 202 for inspection of wafers. In addition, a Virtual Inspection (VI) may be configured to perform mode selection for an inspection recipe using the archived images. Alternatively, the archived images may be provided to another system that is configured to perform mode selection for an inspection recipe using the images. A virtual inspection process is described in detail further herein. Virtual inspection is described in U.S. patent application Ser. No. 12/234,201, filed on Sep. 19, 2008, and is incorporated herein by reference.

In addition, the set of processor nodes may be configured to perform archival of wafer images acquired using BF relatively small pixel inspection. For example, the inspection system 202 is configured as a BF small pixel inspection system, and the set of processor nodes is configured to archive images of wafers generated by the inspection system 202. A "small pixel" is defined herein as a pixel having a size that is less than about 100 nm. Such archived images may also be used to perform one or more applications described herein. For example, in one embodiment, the set of processor nodes is configured to perform offline image analysis of the image data stored in the arrays of the storage media to identify an inspection sample plan for another inspection system that has a lower throughput and higher resolution than the inspection system. Such offline image analysis may be performed using the archived BF relatively small pixel inspection images.

In one embodiment, the set of processor nodes is configured to tune an inspection recipe using the image data stored in the arrays of the storage media. For example, in one embodiment, the set of processor nodes is configured to select one or more defect detection parameters for inspection of the wafer using all of the image data or the selected portion of the image data generated by the detector during the scanning of the wafer that is stored in the arrays of the storage media. The one or more defect detection parameters may include any adjustable parameters of a defect detection method or algorithm (e.g., one or more thresholds). The one or more defect detection parameters may be selected using all of the image data or the selected portion of the image data according to any of the embodiments described herein.

In some embodiments, the set of processor nodes is configured to select one or more defect detection parameters for inspection of the wafer using the image data generated by the detector during the scanning of the wafer that is stored in the arrays of the storage media without requiring additional image data generated by performing additional scanning of the wafer. In this manner, the embodiments described herein enable algorithm tuning using stored data playback thereby freeing up valuable inspection system time that would otherwise be required to rescan the target wafers. In particular, the VI stores wafer images to disk for later playback without the need of a tool or the wafer. The wafer images can be scanned as if the wafer was loaded on the tool thereby allowing users to optimize recipes for a specific optics mode/light level. For example, the inspection system 202 may only be necessary during the mode exploration phase of the recipe optimization process. Once the final mode is selected, the wafer may only be scanned one additional time to save the wafer image to disk. All final recipe optimization may be performed offline with the VI.

Since the set of processor nodes can select one or more defect detection parameters without requiring additional image data generated by performing additional scanning of the wafer, the set of processor nodes can perform offline parametric algorithm tuning. In this manner, the system may be configured for offline recipe setup. In particular, automated inspection system setup conventionally involves iterative inspection (including scanning) of a wafer. Image(s) on a VI can serve as a proxy for the actual wafer thereby relaxing the constraint of having wafer access or a full inspection system with stage and opto-mechanical subsystems. Once the mass image is stored, the user or the system can optimize detection algorithm settings because the VI can operate on the stored images rather than the physical wafer for which the images were acquired.

Using the stored image data for offline recipe setup, "new" defects can be detected by running new inspections without the physical wafer being needed. As such, offline recipe setup may include detecting new defects without the presence of a wafer and an inspection system 202. In this manner, the selection of one or more defect detection parameters can be performed without requiring additional scanning of the wafer and without being limited to those defects that were detected during inspection of the wafer. In particular, since the raw image data is stored, multiple defect detection algorithms can be applied to the raw image data during offline setup, and the multiple defect detection algorithms can be increased in sensitivity such that defects can not only be eliminated by adjusting the one or more defect detection parameters but can also be discovered by adjusting the one or more defect detection parameters.

In one embodiment, defects may be detected on the wafer using the inspection data and a standard reference die for standard reference die based inspection. For example, defect detection may include performing standard reference die based inspection. In some such embodiments, defect detection may include applying mapping of a standard reference die image in design data space to live images acquired by the inspection system for the wafer for standard reference die-to-die inspection mode. The term "standard reference die" generally refers to a reference die on the wafer that is being inspected but does not meet the normal adjacency constraints to the "test" die that are required for die-to-die inspection. Some commercially available inspection systems are configured to use some version of the standard reference die-to-die inspection mode.

One implementation of the standard reference die-to-die inspection mode involves comparing a die to any die within a die row. In another implementation, the standard reference die image may be a stored image. Therefore, stored standard reference die-to-die inspection mode is much like standard reference die-to-die inspection mode, except that the constraint of using a reference die on the wafer is eliminated. One advantage of this inspection mode is that the stored standard reference die image can be modified to make the standard reference die image "substantially defect free." In addition, this inspection mode enables using standard reference die images from a different wafer thereby enabling the simplest implementation of the integrated PWQ (iPWQ) application.

In one embodiment, which may be used for standard reference die-to-die inspection mode, the live image acquired for a die being inspected is aligned to and compared with a stored die image obtained from a known good die (standard reference die) on another wafer. In this case, mapping of the standard reference die pixels to design data coordinate space may be performed completely online. For instance, the alignment sites in the standard reference die may be mapped in the design data space as described above, and the mapped standard reference die pixels may be stored online and fed into the inspection system during inspection. In this manner, for the standard reference die-to-die inspection mode, determining the position of the live inspection data in design data coordinate space may be performed by aligning the live data to the stored standard reference die image or data which itself has been mapped to design space.

In another embodiment, for standard reference die-to-die inspection, a known good die on a reference wafer is scanned at the selected pixel size and imaging mode and the entire known good die image may be stored in an appropriate storage medium (e.g., a disk). During inspection of a wafer, a swath of the appropriate standard reference die image is downloaded into the inspection system image computer, and as each die is scanned, frames of the target die (i.e., the die being inspected) are aligned with the corresponding standard reference die frames. Misalignment between the frames may be corrected using sub-pixel interpolation. The standard reference die image may then the compared to an image of the wafer to detect defects on the wafer (e.g., to detect defective pixel). In this manner, the same image can be used for aligning inspection data to design data space coordinates and for defect detection.

In a different embodiment, the method includes aligning data for the alignment sites on the wafer in the inspection data stream to rendered GDS clips for the predetermined alignment sites to correct errors in real-time. For example, the method may include applying mapping of the rendered GDS II clips in design data space to the data for the alignment sites on the wafer for die-to-die inspection mode. The method may include correlating downloaded alignment site patch images (selected during setup of the inspection process) with the live image data over a predetermined search range and determining the offset between the two images. In another example, aligning data for the alignment sites on the wafer in the inspection data stream to data for the predetermined alignment sites may be performed by aligning a centroid or other attribute of one or more features in the alignment sites, which may be performed as described further herein. In one embodiment, for defect detection in die-to-die inspection mode, data for each scanned die frame is aligned with data for the subsequent die frame in the swath. In this case, mapping of the predetermined alignment sites and the alignment sites on the wafer may not be performed offline since the position of the data for each die in the inspection data stream is subject to mechanical and other error sources of the inspection system. Therefore, in this case, the method may include identifying the alignment sites in each die (e.g., using the image computer) during the acquisition of the inspection data.

In some embodiments, defect information may be aligned with electrical design. For example, a scanning electron microscope (SEM) review system may be used to determine more accurate coordinates of defect locations for a sample of defects, and the defect coordinates reported by the SEM review system may be used to determine locations of defects in the electrical design. In other embodiments, inspection care areas (e.g., the areas of the device pattern formed on the wafer in which inspection will be performed) may be aligned to the physical location of the pattern printed on the wafer.

In a fourth step 308, one or more overlay sites of a selected predetermined pattern of a semiconductor wafer exceeding a selected overlay error level may be identified utilizing a defect inspection technique.

In one aspect, a predetermined pattern for an overlay metrology measurement of a semiconductor wafer 206 may be selected. The overlay sites of a selected predetermined pattern of the semiconductor wafer 206 may be detected using any suitable inspection process and any suitable inspection system 202. For example, the inspection results may be acquired using a bright-field (BF) inspection system, dark-field (DF) inspection system or an electron beam inspection system. Moreover, the results of the inspection by the inspection system 202 may include overlay site locations, sizes, images of the sites, or any other output generated by an inspection system. Moreover, the overlay sites of the selected predetermined pattern of the semiconductor wafer may be detected using a virtual inspection (VI) process. As stated previously, a virtual inspection process is described in detail further herein. Virtual inspection is described in U.S. patent application Ser. No. 12/234,201, filed on Sep. 19, 2008, and is incorporated above by reference.

One or more locations for overlay metrology measurement may be located within a selected pattern on a semiconductor wafer 206. In one embodiment, the selected pattern in which one or more overlay sites may reside may be formed at multiple locations on the semiconductor wafer. In another embodiment, the pattern may include only a portion of an entire design patterned on the wafer. For example, a die formed on the semiconductor wafer may include a number of different patterns, and the selected pattern may include one specific pattern that forms only a portion of a die formed on the wafer. Therefore, the selected pattern may be formed in each die formed on the wafer. For instance, at least one instance of the selected pattern may be formed in each die on the wafer. Moreover, each die may include more than one instance of the selected pattern. Thus, the selected pattern may be formed at multiple instances in a die and in more than one die formed on the semiconductor wafer.

In an additional embodiment, the selected pattern may include a POI. The POI may be selected by a user. For instance, a user may manually select a POI. In another instance, a user may select a POI via a pre-programmed computer system.

In one embodiment, the predetermined pattern includes a pattern that is more sensitive to process variations than another pattern on the wafer. For example, in one such embodiment, a pattern that is more sensitive to process variations than another pattern may be determined based on experimental results (e.g., inspection results, defect review results, metrology results, failure analysis results, etc. generated for wafers containing the pattern). In another such embodiment, a pattern that is more sensitive to process variations than other patterns on the wafer may be determined based on empirical data (e.g., information about one or more attributes of the patterns formed on the wafer such as dimension, spacing, pattern density, etc.). Such empirical data may be acquired in any manner known in the art (e.g., from design data for the wafer). In this manner, in some embodiments, the method includes identifying the predetermined pattern using design data for the wafer.

In a fifth step 310, the locations of the defects detected in step 306 may be compared to the identified overlay site positions identified in step 308 in order to identify locations wherein a defect is in proximity to an identified overlay site.

For example, the locations of defects detected within a care area may be reported by an inspection system 202. In addition, the location of the potential overlay sites of a predetermined pattern may be reported using methods described herein. Therefore, the locations of the defects within a care area on the wafer and the locations of the potential overlay sites within a care area may be compared. For instance, the x and y coordinates of the detected defects may be compared to the x and y coordinates of the overlay sites. Further, this comparison may be performed in any suitable manner, and the locations wherein a detected defect and a potential overlay site are in close proximity may be identified.

Figure 4A:
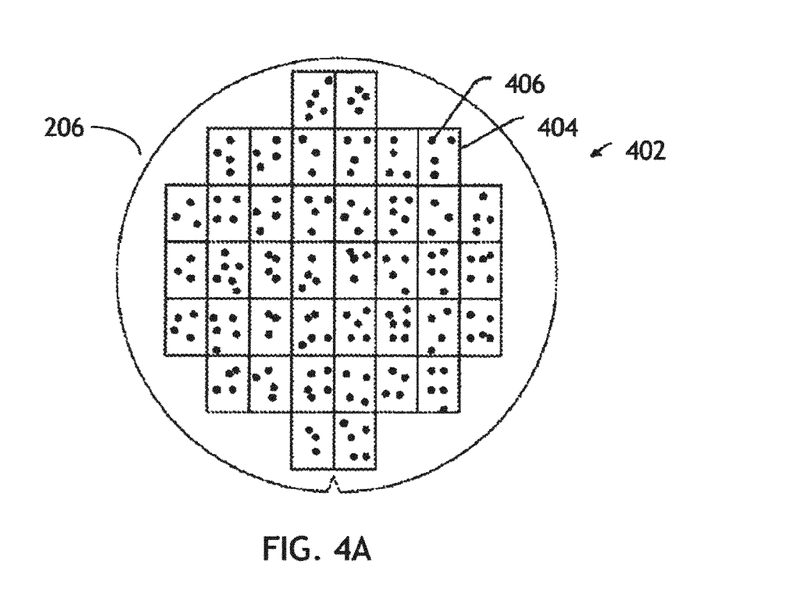
FIG. 4A illustrates an exemplary inspection result of a semiconductor wafer suitable for implementation in the present invention.

FIG. 4A illustrates one example of results of inspection of a wafer that may be used by embodiments described herein. In particular, the results of the inspection shown in FIG. 4A include a wafer map 402. Wafer map 402 includes rectangles 404 corresponding to the dies on the wafer. In particular, each of the rectangles in the wafer map indicates a die formed on the wafer. Therefore, although a particular number of rectangles is shown in FIG. 4A in one particular arrangement, it is to be understood that the number and arrangement of the rectangles on the wafer map will vary depending on the design for the wafer and the layout of the dies on the wafer. In addition, wafer map 402 includes symbols 406, each of which indicates the position of a defect detected on the wafer. Although a particular number of symbols is shown in FIG. 4A in one particular arrangement, it is to be understood that the number and arrangement of the symbols on the wafer map will vary depending on the inspection results for the wafer (e.g., the defects detected by inspection). If such a wafer map is included in the results of the inspection of the wafer or generated by the embodiments described herein, the locations of the predetermined pattern on the wafer may be overlaid on wafer map 402, and defects that are located within the predetermined pattern or that have locations that at least partially overlap with the locations of the predetermined pattern can be identified in the map. Moreover, the locations of the potential overlay sites may be identified within the identified predetermined patterns, then allowing the comparison of the location of the defects within a predetermined pattern to the potential overlay sites of the predetermined pattern.

Figure 4B:
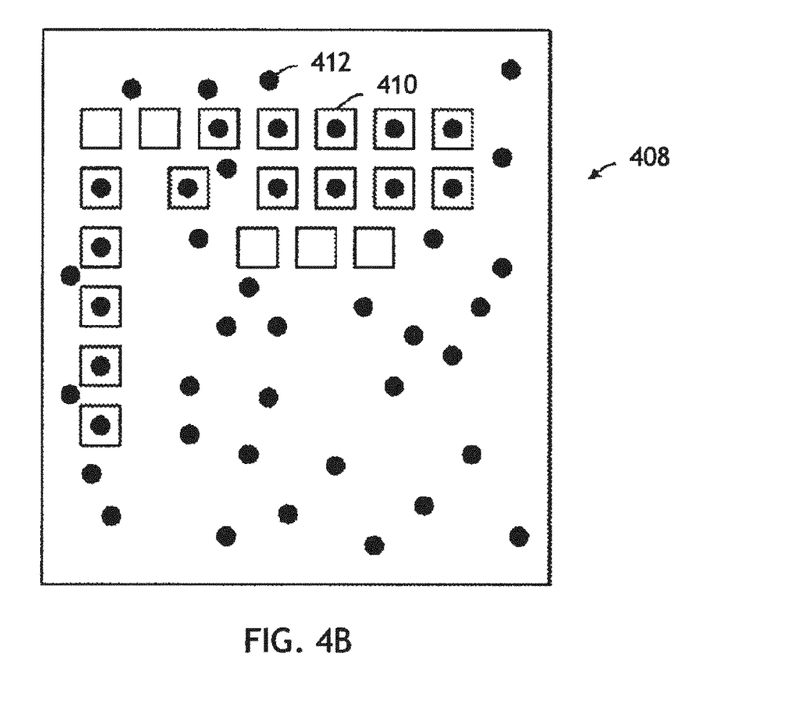
FIG. 4B illustrates exemplary results of comparing detected defect location data to identified overlay metrology site location data in a generated care area.

FIG. 4B illustrates one example of results of one embodiment of overlaying results of inspection of a wafer with locations of a predetermined pattern on the wafer. In particular, FIG. 4B illustrates map 408 of one die formed on a wafer. The map of the die may be included in and extracted from a wafer map such as that shown in FIG. 4A. Map 408 includes rectangles 410 corresponding to the identified overlay metrology sites of a selected predetermine pattern. In particular, each of the rectangles in map 408 corresponds to one instance of an identified overlay metrology site. Therefore, although a particular number of rectangles are shown in FIG. 4B in one particular arrangement, it is to be understood that the number and arrangement of the rectangles within the die will vary depending on the design for the wafer.

Map 408 also includes symbols 412, each of which indicates the position of a detected defect. Although a particular number of symbols is shown in FIG. 4B in one particular arrangement, it is to be understood that the number and arrangement of the symbols within the map will vary depending on the results of the inspection (e.g., the defects detected by inspection). Therefore, map 408 illustrates the locations of the identified potential overlay metrology sites 410 within a care area of a die overlaid with the locations of the defects 412 detected within a care area of a die. As such, defects that are located within or near an overlay site may be identified in the map as those defects corresponding to the symbols that are located at least partially within one of the rectangles.

In a sixth step 312, a metrology sampling plan may be generated utilizing the locations identified in step 310 wherein a defect is proximate to an identified overlay site.

In one embodiment, step 312 includes generating the metrology sampling plan based on results of locations identified in step 310 wherein a defect is proximate to an identified overlay site such that one or more areas on the wafer in which the one or more identified individual defects are located are sampled during metrology. In addition, the method includes generating a metrology sampling procedure that takes into account defect inspection data that shows potential overlay error sites and design context. For example, as described further herein, inspection data such as BF inspection data can be used to identify potential overlay metrology sites on the wafer, and the metrology sampling plan can be generated such that measurements such as CD measurements are performed at these overlay sites during metrology. In this manner, a CD sampling plan may be generated for sampling of the outliers.

The metrology sampling plan may be generated in any suitable format (such as a file format that can be used by a metrology system 204). In addition, the metrology sampling plan may be generated by creating a new metrology sampling plan that includes the one or more areas on the wafer in which the one or more identified defects proximate to an overlay site are located as the areas to be sampled or altering an existing metrology sampling plan by changing the samples areas in the existing plan to the one or more areas on the wafer in which the one or more identified defects proximate to an overlay site are located.

In one embodiment, the method includes performing the method separately for different predetermined patterns on the wafer such that different metrology sampling plans are generated for the different predetermined patterns. For example, different metrology sampling plans may be generated for two or more different predetermined patterns as described herein in the same method (e.g., simultaneously and separately). Therefore, the sampling plan for each of the different predetermined patterns (e.g., some or all of the different patterns formed on the wafer) may be determined based on the identified overlay sites located only in the corresponding predetermined patterns.

Sampling plans for different predetermined patterns (or any single predetermined pattern) may also be generated based on the priority of the different predetermined patterns. For example, the priority assigned to different predetermined patterns may be based on the criticality of the predetermined patterns as well as other characteristics of the predetermined patterns (e.g., yield relevance). The priority of different predetermined patterns may be determined and assigned as described in the patent applications by Kulkarni et al. and Zafar et al., which are incorporated by reference above. Therefore, a sampling plan for a predetermined pattern that has a higher priority may include more sampling sites than a sampling plan for a predetermined pattern that has a lower priority. In this manner, different predetermined patterns on a single wafer can be sampled more or less heavily based on the priority assigned to the predetermined patterns. As such, more or less information can be acquired for the different predetermined patterns based on the priority assigned to the patterns such that more information is acquired during metrology for the higher priority predetermined patterns than the lower priority predetermined patterns. As a result, the metrology sampling plans generated as described herein may be used to acquire metrology results that are particularly relevant to yield thereby increasing the value of the metrology results while possibly also decreasing the time and cost involved in acquiring the metrology results.

In another embodiment, generating the metrology sampling plan is performed dynamically. For example, the embodiments described herein can use inspection data to create dynamic sampling (e.g., for CD measurements). In particular, since the metrology sampling plans are generated as described herein based on results of inspection of the wafer (e.g., based on information about the overlay sites and defects located in predetermined patterns formed on the wafer), a metrology sampling plan can be generated for each wafer for which inspection results have been generated. In some embodiments, therefore, generating the metrology sampling plan is performed on a wafer-to-wafer basis. As such, the metrology sampling plans can be generated as described herein dynamically such that measurements can be performed at dynamically determined sampling locations instead of the fixed locations at which CD measurements are performed based on currently used metrology sampling plans.

In a further step, overlay error may be measured at the locations identified in step 310, wherein a defect is proximate to an identified overlay site, utilizing the generated metrology sampling plan generated in step 312. For example, any known metrology process and metrology system may be utilized to measure overlay error at the identified locations. For instance, the metrology system 204 may be used to measure overlay error at the locations identified in step 310.

In one embodiment, the metrology includes CD metrology. However, as mentioned above, the metrology may include any suitable metrology process, which may include performing any suitable measurements using any suitable metrology system 204. For example, the metrology process may include measuring CD using a scatterometry system. In another example, the metrology process may include measuring roughness using an atomic force microscope (AFM). In yet another example, the metrology process may include measuring profile of the defects using a scanning electron microscope (SEM). In addition, the metrology may include performing one or more different measurements of the defects using one or more measurement techniques. The methods described herein also may or may not include performing metrology of the wafer using the metrology sampling plan generated as described herein. For example, the metrology sampling plan may be used by the embodiments described herein or another system or method to perform metrology of the wafer.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method generates the metrology sampling plan, the method may include storing the metrology sampling plan in a metrology recipe in a storage medium. In addition, results or output of the embodiments described herein may be stored and accessed by a metrology system such as a CD SEM such that the metrology system 204 can use the metrology sampling plan for metrology assuming that the output file can be understood by the metrology system. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

The metrology sampling plans generated by the embodiments described herein provide a number of advantages over other metrology sampling plans such as fixed sampling plans. For instance, the metrology sampling plans generated as described herein will result in much improved selection of metrology sites (e.g., CD sites) that would signal subtle changes (e.g., in CD) for better detection of variations (e.g., CD variations). The metrology sampling plans generated as described herein would also increase the chance of detecting variations (e.g., CD variations) that traditional approaches may miss.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for inspection guided metrology, comprising:
   performing a pattern search in order to identify one or more instances of a predetermined pattern on a semiconductor wafer;
   generating a care area for each of the one or more instances of the predetermined pattern on the semiconductor wafer;
   identifying one or more defects within each of the one or more generated care areas by performing an inspection scan of each of the one or more generated care areas, wherein the inspection scan includes a low-threshold inspection scan or a high sensitivity inspection scan;
   identifying one or more metrology sites of at least some of the one or more instances of the predetermined pattern on the semiconductor wafer having a measured metrology parameter deviating from a selected metrology specification utilizing a defect inspection technique;
   comparing location data of the one or more identified defects of a generated care area to location data of the one or more identified metrology sites within the generated care area in order to identify one or more locations wherein the one or more defects are proximate to the one or more identified metrology sites; and
   generating a metrology sampling plan based on the identified one or more locations wherein the one or more defects are proximate to the one or more identified metrology sites.

2. The method of claim 1, wherein the defect inspection technique comprises:
   a virtual inspection technique.

3. The method of claim 1, wherein the defect inspection technique includes one of the group including a bright-field inspection technique, a dark-field inspection technique, and an electron beam inspection technique.

4. The method of claim 1, wherein the predetermined pattern of the semiconductor wafer is formed at multiple locations on the semiconductor wafer.

5. The method of claim 1, wherein the predetermined pattern of the semiconductor wafer is a pattern of interest (POI).

6. The method of claim 1, further comprising:
   selecting the predetermined pattern for a metrology measurement of a semiconductor wafer.

7. The method of claim 1, wherein the generating a care area for each of the one or more instances of the predetermined pattern on the semiconductor wafer comprises:
   generating a care area for each of the one or more instances of the predetermined pattern on the semiconductor wafer utilizing a context based inspection process.

8. The method of claim 7, wherein the generating a care area for each of the one or more instances of the predetermined pattern on the semiconductor wafer utilizing a context based inspection process comprises:
   selecting a region of interest in a full die image;
   extracting a design from the selected region of interest;
   extracting one or more hot spots for the extracted design; and
   generating a care area for the extracted hot spots.

9. The method of claim 1, wherein the generating a care area for each of the one or more instances of the predetermined pattern on the semiconductor wafer comprises:
   generating a care area for each of the one or more instances of the predetermined pattern on the semiconductor wafer based on one or more results of a cell names search process.

10. The method of claim 1, wherein the performing a pattern search in order to identify one or more instances of a predetermined pattern on a semiconductor wafer comprises:
    performing a pattern search in order to identify one or more instances of a predetermined pattern on a semiconductor wafer utilizing design data of the semiconductor wafer.

11. The method of claim 1, wherein the performing a pattern search in order to identify one or more instances of a predetermined pattern on a semiconductor wafer comprises:
    performing a pattern search in order to identify one or more instances of a predetermined pattern on a semiconductor wafer utilizing a design based binning technique.

12. The method of claim 11, wherein the performing a pattern search in order to identify one or more instances of a predetermined pattern on a semiconductor wafer utilizing a design based binning technique comprises:
    performing a pattern search in order to identify one or more instances of a predetermined pattern on a semiconductor wafer by binning defects detected on the wafer in groups such that portions of design data proximate positions of the defects in each of the groups are at least similar.

13. The method of claim 1, wherein the identifying one or more defects within each of the one or more generated care areas by performing an inspection scan of each of the one or more generated care areas, wherein the inspection scan includes a low-threshold inspection scan or a high sensitivity inspection scan, comprises:

identifying one or more defects within each of the one or more generated care areas by performing an inspection scan of each of the one or more generated care areas, wherein the inspection scan is performed on each of the one or more generated care areas utilizing an inspection recipe optimized for each of the one or more generated care areas.

14. The method of claim 1, wherein the generated metrology sampling plan is suitable for at least one of critical dimension metrology and overlay metrology.

15. The method of claim 1, wherein generating a metrology sampling plan based on the identified one or more locations wherein the one or more defects are proximate to the one or more identified metrology sites comprises:

dynamically generating a metrology sampling plan based on the identified one or more locations wherein the one or more defects are proximate to the one or more identified metrology sites.

16. The method of claim 1, further comprising:

measuring a metrology parameter at the identified one or more locations wherein the one or more defects are proximate to the one or more identified metrology sites utilizing the generated metrology sampling plan.

17. The method of claim 1, wherein the identifying one or more metrology sites of at least some of the one or more instances of the predetermined pattern on the semiconductor wafer having a measured metrology parameter deviating from a selected metrology specification utilizing a defect inspection technique comprises:

identifying one or more metrology sites of at least some of the one or more instances of the predetermined pattern on the semiconductor wafer having at least one of a measured focus parameter and dose parameter deviating from a selected metrology specification utilizing a defect inspection technique.

18. A system for inspection guided metrology, comprising:

an inspection system configured to detect defects on a semiconductor wafer;

a metrology system configured to measure a metrology parameter at one or more locations of a selected pattern on a semiconductor wafer; and a computer system configured to:

perform a pattern search in order to identify one or more instances of a predetermined pattern on a semiconductor wafer;

generate a care area for each of the one or more instances of the predetermined pattern on the semiconductor wafer;

identify one or more defects within each of the one or more generated care areas by performing an inspection scan of each of the one or more generated care areas, wherein the inspection scan includes a low-threshold inspection scan or a high sensitivity inspection scan;

identify one or more metrology sites of at least some of the one or more instances of the predetermined pattern of the semiconductor wafer having a measured metrology parameter deviating from a selected metrology specification utilizing a defect inspection technique;

compare location data of the one or more identified defects of a generated care area to location data of the one or more identified metrology sites within the generated care area in order to identify one or more locations wherein the one or more defects are proximate to the one or more identified metrology sites; and generate a metrology sampling plan based on the identified one or more locations wherein the one or more defects are proximate to the one or more identified metrology sites.

19. The system of claim 18, wherein the inspection system includes one of the group including a bright-field inspection system, a dark-field inspection system, and an electron beam inspection system.

20. The system of claim 18, wherein the metrology system is configured to perform at least one of critical dimension metrology and overlay metrology.

21. The system of claim 18, wherein the metrology system is configured to utilize the generated metrology sampling plan.

22. The system of claim 18, wherein the metrology system and the inspection system are configured to operate utilizing a common coordinate system.

23. The system of claim 18, wherein the computer system is configured to utilize design data of the semiconductor wafer in order to correlate location data of the one or more identified defects of a generated care area to location data of the one or more identified metrology sites within the generated care area.

24. The system of claim 18, wherein the metrology system is configured to measure at least one of focus and dose.

\* \* \* \* \*